United States Patent [19]

Stoll

[11] Patent Number: 5,585,118
[45] Date of Patent: Dec. 17, 1996

[54] CHOLINE IN THE TREATMENT OF BIPOLAR DISORDER

[75] Inventor: Andrew L. Stoll, Lincoln, Mass.

[73] Assignee: Brigham and Women's Hospital, Boston, Mass.

[21] Appl. No.: 460,060

[22] Filed: Jun. 2, 1995

[51] Int. Cl.$^6$ .................. A61K 33/00; A61K 31/685
[52] U.S. Cl. ................. 424/722; 424/715; 514/77; 514/78; 514/76
[58] Field of Search .................. 424/677, 722, 424/715; 514/77, 78, 76

[56] References Cited

U.S. PATENT DOCUMENTS 4,346,084   8/1982   Growdon et al. ............ 424/677

OTHER PUBLICATIONS

Charles et al., "Elevated Choline Concentrations in Basal Ganglia of Depressed Patients," *Bio. Phsychiatry* 31:99A, abstr. #86 (1992).
Cohen et al., "Lecithin in the Treatment of Mania: Double-Blind, Placebo-Controlled Trials," *Am. J. Psychiatry* 139:1162–1164 (1982).
Cohen et al., "Lecithin in Mania: A Preliminary Report," *Am. J. Psychiatry* 137:242–243 (1980).
Cornatzer et al., "The Effect of Hyper and Hypothyroidism, Hypophysectomy and Adrenalectomy on Phosphatidylethanolamine Methyltransferase, Phosphatidyldimethyl–Ethanolamine Methyltransferase and Choline Phosphotransferase of Rat Liver Microsomes," *Int. J. biochem.* 16:567–570 (1984).
Dawson et al., "The Inhibition of Diacylglycerol–Stimulated Intracellular Phospholipases by Phospholipids with a Phosphocholine–Containing Polar Group," *Biochem. J.* 230:61–68 (1985).
Happe et al., "High–Affinity Choline Transport Sites: Use of [$^3$H]Hemicholinium–3 As a Quantitative Marker," *J. Neurochem.* 60:1191–1201 (1993).
Janowsky et al., "A Cholinergic–Adrenergic Hypothesis of Mania and Depression," *The Lancet* 632–635 (Sep. 23, 1972).
Leiva, "The Neurochemistry of Mania: A Hypothesis of Etiology and a Rationale for Treatment," *Prog. Neuro–Psychopharmacol. & Bio. Psychiat.* 14:423–429 (1990).
Millington et al., "Lithium Administration Potentiates the Effect of Exogenous Choline on Brian Acetylcholine Levels," *Nutrition and the Brain* 5:417–424 (1979).
Millington et al., "Lithium and Brain Choline Levels," *New Eng. J. Med.* 300: 196–197, Letter to the Editor (1979).
Millington et al., "Choline Administration Elevates Brain Phosphorylcholine Concentrations," *J. Neurochem.* 38: 1748–1752.
Roy–Byrne et al., "Approaches to the Evaluation and Treatment of Rapid–Cycling Affective Illness," *British J. Psychiat.* 145:543–550 (1984).
Sands et al., "The Role of a Phosphatidylcholine–Specific Phospholipase C in the Production of Diacylglycerol for Nitric Oxide Synthesis in Macrophages Activated by IFN–$\delta$ and LPS," *Biochem. Biophys. Res. Comm.* 199:461–466 (1994).
Schreier, "Mania Responsive to Lecithin in a 13–Year Old Girl," *Am. J. Psychiatry* 139:108–110 (1982).
Stoll et al., "Choline Ingestion Increases the Resonance of Choline–Containing Compounds in Human Brain: An In Vivo Proton Magnetic Resonance Study," *Biol. Psychiatry* 37:170–174 (1995).
Stoll et al., "Erythrocyte Choline Concentrations in Psychiatric Disorders," *Biol. Psychiatry* 29:309–321 (1991).
Tamminga et al., "Depression Associated with Oral Choline," *The Lancet* 905, Letter to the Editor (Oct. 23, 1976).
Toide et al., "Effects of a Novel Thyrotropin–Releasing Hormone Analogue, JTP–2942, on Extracellular Acetylcholine and Choline Levels in the Rat Frontal Cortex and Hippocampus," *Eur. J. Pharmacol.* 233:21–28 (1993).

*Primary Examiner*—Raymond Henley, III
*Attorney, Agent, or Firm*—Michael A. Sanzo; Vinson & Elkins

[57] ABSTRACT

The present invention is directed to methods in which a lithium source and a choline source act synergistically to reduce or eliminate the symptoms associated with bipolar disorder.

18 Claims, 6 Drawing Sheets

CHOLINE IN THE TREATMENT OF BIPOLAR DISORDER

FIELD OF THE INVENTION

The present invention relates to medical treatments for psychiatric disorders. More specifically, it deals with novel methods and compositions useful in treating patients with bipolar disorder.

BACKGROUND OF THE INVENTION

Patients with bipolar disorder suffer recurrent, alternating cycles of mania and depression. A number of anecdotal reports have suggested that lecithin (phosphotidylcholine), a dietary precursor of choline, has anti-manic properties that might be useful in treating patients with this disorder (Cohen et al., *Am. J. Psychiatry* 137:242–243 (1980); Schreier, *Am. J. Psychiatry* 139:108–110 (1982); Leiva, *Prog. Neuro-Psychopharmacol. & Biol. Psychiat.* 14:423–429 (1990)). In addition, a controlled clinical study performed more than a decade ago reported that lecithin has a modest anti-manic effects when given to patients with bipolar illness (Cohen et al., *Am. J. Psychiatry* 139:1162–1164 (1982)).

At the time that lecithin administration was begun in the 1982 clinical study by Cohen et al., many patients were taking other medications, including lithium. The patients continued on such medications during the course of the study but no attempt was made to identify particular drugs that might contribute to the observed beneficial effects of lecithin. The possibility that lithium might be essential to the effect was not appreciated. In addition, it was uncertain, both from this paper as well as from the anecdotal reports mentioned above, whether the beneficial effects observed with lecithin were due to choline derived from the digestion of the compound. Lecithin is a major component of cellular membranes and the possibility was recognized that lecithin might be exerting its effects on mania by causing alterations in the membranes of neural cells (Cohen et at., *Am. J. Psychiatry* 139:1162–1164 (1982)).

The present inventors recently conducted an open, post-hoc reevaluation of the raw data from Cohen's open and double-blind lecithin trials (Cohen et al., *Am. J. Psychiatry* 139:1162–1164 (1982)). This revealed that it was only those patients who received concurrent lithium with lecithin who showed a substantial and consistent lessening of symptoms associated with mania. Thus, the reevaluation suggested the possibility that lecithin might be exerting its beneficial effect by providing a source of choline which then acts in concert with lithium.

In terms of providing a source of therapeutic choline, lecithin has two main drawbacks. First, lecithin must be broken down into choline by in vivo biochemical processes whose efficiency may vary from individual to individual. Thus, the dosage of choline delivered to different patients by a given concentration of lecithin cannot be accurately predicted. A second problem with the therapeutic use of lecithin stems from its being a phospholipid and the fact that obtaining a beneficial effect on mania has often entailed giving patients very large (15–30 grams) of lecithin per day (see e.g. Cohen et al., *Am. J. Psychiatry* 137:242–243 (1980); Schreier, *Am. J. Psychiatry* 139:108–110 (1982)). The intake of such a large quantity of lipid for therapeutic purposes may promote cardiovascular disease or obesity.

The inventors discovered that the concentration of brain choline in humans can be increased by the administration of a salt of choline when the salt is given at a dose of about 50 mg of free choline per kg body weight per day (see Example 1 below; see also, Stoll et al., *Biol. Psychiatry* 37:170–174 (1995); Stoll et al., Biol. Psychiatry 29:309–321 (1991); Millington et al., *NEJM* 300:196–197 (1979); Millington et at., Barbeau A (eds) Vol. 5, Raven Press, New York (1979)). This observation, together with the results of the reevaluation of Cohen's lecithin trials and similar considerations, led to the present invention which is directed to methods and compositions for treating patients with bipolar disorder and in which lithium is administered concomitantly with a source of choline other than lecithin. The inventors have demonstrated the effectiveness of this approach on patients with the most severe forms of the illness: rapid cycling and lithium-refractory bipolar disorder.

SUMMARY OF THE INVENTION

The present invention is based upon the discovery that lithium and choline can be used in combination to stabilize the mood fluctuations of a patient with bipolar disorder. In particular, the invention provides for a method of treating bipolar disorder administering a lithium source in combination with a choline source and in which these agents are periodically administered in amounts effective to reduce or eliminate the symptoms associated with the disorder and the administration of these agents is continued during both the manic and depressive phase of the disorder. As an initial concentration, it is preferred that choline be administered at a dose of about 50 mg of free choline per kg of patient body weight per day. This concentration may be adjusted in order to maximize the efficacy of the treatment. After adjustment, a patient should receive between 2 and 8 grams of free choline per day. Favorable results may be obtained even with lithium refractory bipolar disorder and particularly malignant forms of bipolar disorder such as rapid-cycling bipolar disorder. It is preferred that choline be administered orally in the form of choline bitartrate. Optionally, the method may further comprise measuring the choline levels in the brain of patients using magnetic resonance spectroscopy.

In instances where a patient with bipolar disorder is receiving very high dose thyroid medication, such as thyroxine, it is preferred that the thyroid medication be reduced or eliminated while concurrently administering the combination of choline and lithium. Again, choline should be administered at a dose of about 50 mg of free choline per kg of patient body weight per day and adjusted to a final concentration of between 2 and 8 grams of free choline per day. It is preferable that choline be given orally in the form of choline bitartrate.

BRIEF DESCRIPTION OF THE FIGURES

FIG. 1 shows the change in brain choline/creatine resonance with respect to time in 4 healthy volunteers after the ingestion of 50 mg/kg of oral choline. Each line represents the results for a different volunteer. Details of study methodology are set forth in Example 1 below.

FIG. 2 shows the percentage change in brain choline/creatine resonance after the oral administration of choline and lithium. It can be seen that the brain choline resonance rose dramatically in all responders, i.e. in all patients experiencing a reduction in the number or severity of mood alterations in response to the choline/lithium therapy. The end point was one week for all cases, except for 5 and 6, as described in the text. The patients in these cases were both receiving supra therapeutic thyroxine. In case 6, thyroxine administration to the patient was discontinued and the patient subsequently responded to the combination of choline and lithium. The figure shows the rise in the choline/creatine ratio of this patient observed after discontinuation of thyroxine.

FIGS. 3–6 show the mood ratings recorded by patients before and during choline treatment. Mood ratings were performed by the patient twice daily (for best and worst mood) using a standard form. FIG. 3 shows the results recorded by the patient in case 1; FIG. 4 shows the results recorded in case 2; FIG. 5 shows the results recorded in case 3; and FIG. 6 shows the results recorded in case 6. FIG. 6 differs from the others in that, at the time choline administration was initiated, the patient was receiving supra-therapeutic thyroxine. Thus, mood ratings were recorded both before and after thyroxine reduction.

DETAILED DESCRIPTION OF THE INVENTION

Figure 1:
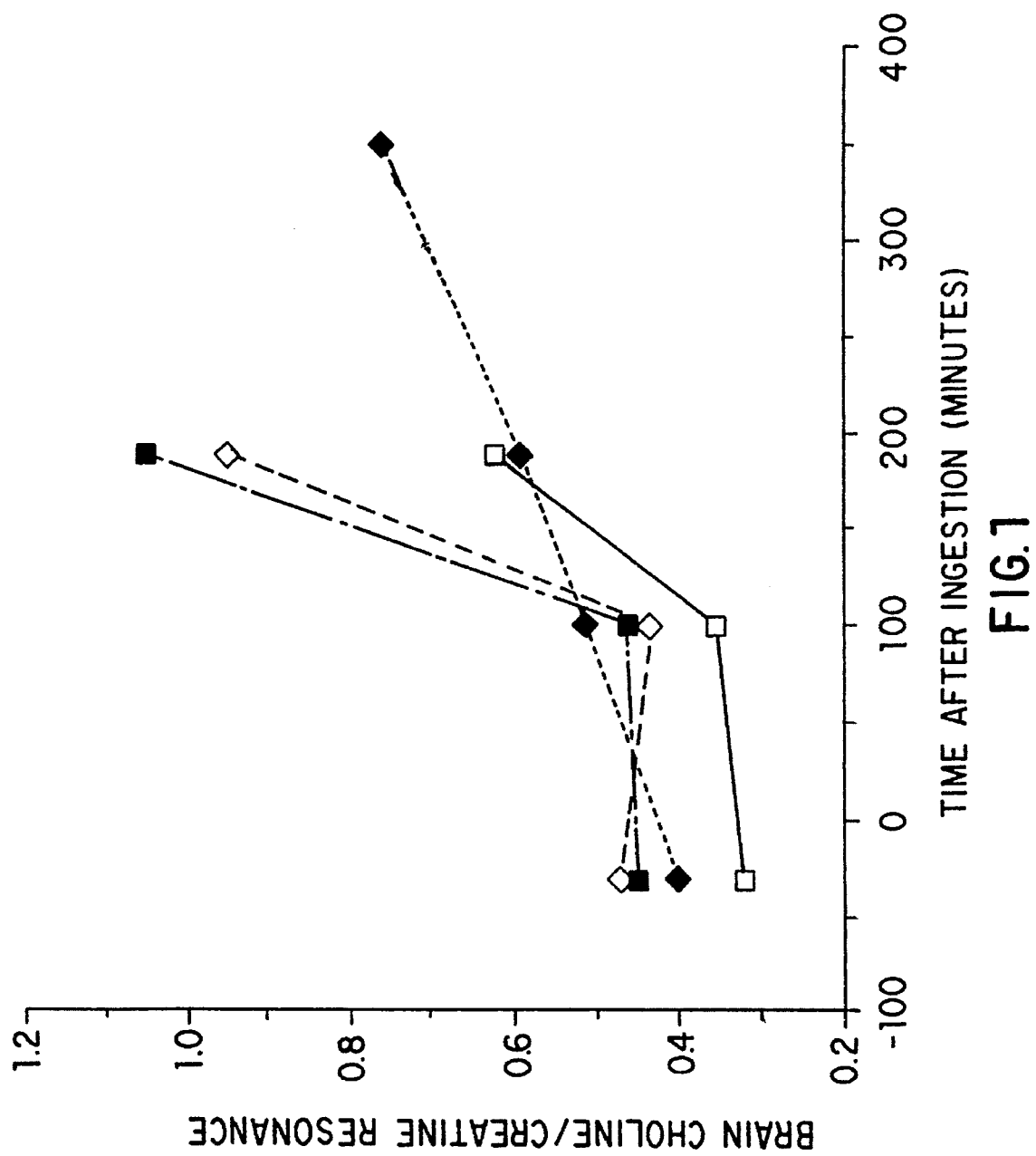
FIG. 1.

In the following description, reference will be made to various methodologies well-known to those skilled in the art of medicine and pharmacology. Standard reference works setting forth general principles of these disciplines include: Goodwin, F. K. and Jamison, K. R., *Manic. Depressive Illness*, Oxford University Press (1990); and Bloom, F. and Kupfer, D., *Psychopharmacology, The Fourth Generation of Progress*, Raven Press (1994).

A. Definitions

Bipolar disorder: Bipolar disorder refers to a brain illness, often hereditary, characterized by abnormally severe mood swings. The patient alternates between episodes of mania and episodes of depression. Approximately 1–2 % of the population suffers from this often disabling illness.

Rapid cyclic bipolar disorder: Rapid cycling bipolar disorder is a form of the illness characterized by the high frequency at which patients undergo cycles of mood alteration. Patients exhibiting four or more mood episodes in one year are considered to have rapid cycling disorder. Approximately one in five patients with bipolar disorder have the rapid cycling form.

Lithium-refractory bipolar disorder: Approximately 50 to 60% of bipolar patients do not respond fully to lithium therapy. Because of its prevalence, this "lithium-refractory" or "lithium-resistant" form of bipolar disorder presents a major clinical problem.

Choline: Choline (hydroxyethyl trimethyl ammonium hydroxide) is considered to be a vitamin of the B complex and is derivable from many foods. Unless otherwise indicated, the term "choline", as used herein, refers not only to the isolated choline molecule (i.e. free choline) but also to any biologically compatible salt of choline (e.g., choline bitartrate). Any sources of choline may be used in the invention provided that it delivers a dosage of free choline that is reasonably predictable and provided that it does not cause unacceptable side effects. In this regard, it should be noted that the source of choline used in the present methods and compositions should not have lecithin as its sole or primary component.

Lithium: Unless otherwise indicated, the term "lithium" refers to any salt containing lithium as the cationic component.

B. Method of Treating Patients Using Choline in Combination with Lithium

The present invention is directed to the treatment of bipolar disorder using a combination of lithium and choline.

These agents may be given together in a single dosage form or supplied separately. It will be appreciated that many different procedures may be used in tailoring this therapy to individual patients. The following paragraphs describe the preferred, but not exclusive, method.

In many instances, patients administered choline according to the invention will already have been diagnosed as having bipolar disorder and will be receiving lithium at the time that choline treatment is initiated. If the lithium dosage appears to be in need of adjustment, this should generally be done before choline administration is started (see generally, Bloom, F. and Kupfer, D., *Psychopharmacology. The Fourth Generation of Progress*, Raven Press (1994)). Otherwise, the lithium medication of the patient should be maintained and, subject to consideration of possible adverse side effects as discussed below, choline should be administered at an initial dose of about 50 mg of free choline per kg of body weight. As set forth in detail in the appended examples, an acceptable regime is to initially administer between 6 and 12 capsules of choline bitartrate per day, each capsule containing 780 mg of the salt. Since 780 mg of choline bitartrate provides 350 mg of free choline, the patient initially receives a total daily dose of between 2.7 and 5.4 grams of free choline. Preferably this total daily dose is divided into several smaller doses administered at regular intervals during the day. Most preferably patients are administered choline in a split BID dosage schedule, e.g., two 25 mg/kg doses of choline may be given each day.

In instances in which a patient is taking multiple drugs or in which there is some reason to believe that they may be unusually sensitive to choline, it may be desirable to start with a much lower initial dose of free choline, e.g. between 1 and 2 grams, in order to ensure that the patient is able to tolerate the medication without unacceptable side effects. Once this is established, the dosage may be adjusted upward. During this time, the administration of lithium should be maintained.

The effect of the initial daily dosage on mood alterations should be evaluated by the patient over a period of time, e.g. one to 4 weeks. One good way to carry out this evaluation is for patients to keep a daily record in which they chart their moods. As set forth in the examples, charts in which patients rate their best and worst daily mood state as normal; mildly, moderately or severely depressed; or mildly, moderately, or severely manic, can be effectively used. This diary should help the patient and their physician to determine if mood fluctuations are becoming less frequent or less extreme. Ideally, such a record should be kept both before and after the administration of choline is begun. The evaluation of mood alterations by the patient may be supplemented by magnetic resonance spectroscopy performed both before choline treatment is initiated and at the end of the patient evaluation period (see, Example 1 below; and Stoll et al., *Biol. Psychiatry* 37:170–174 (1995)). The MRS results should reveal whether there has been an increase in brain choline concentration. If there has not been an improvement in mood fluctuations and brain choline resonance is not elevated, choline dosage should be increased (again, provided that there are not unacceptable side effects).

In some cases, the evaluation discussed above may indicate that mood fluctuations have become so stabilized that no adjustment in choline dosage is necessary. In other cases, the dosage of free choline administered may be increased in order to obtain a more efficacious result. As set forth in the appended examples, increasing initial dosages to a level of between 2 and 8 grams per day after about a week of patient evaluation was found to be an acceptable procedure. As the dosage of choline administered increases, it becomes increasingly likely that a patient will experience side effects such as diarrhea, abdominal discomfort, or the development of a fishy body odor due to the breakdown of choline into trimethylamine by gut bacteria. In these instances, it may be desirable to reduce the concentration of administered choline in order to decrease the severity of the side effect.

The process of adjusting dosages in an upward or downward direction and evaluating the effect of the adjustment on mood changes should be continued until an optimum dosage is discovered, i.e. the dosage at which the patient experiences the best balance between therapeutic effectiveness and discomfort. In cases where adverse side effects are not experienced, the optimal dosage is the lowest dose resulting in maximum stabilization of mood fluctuation.

The same basic procedure described above can be used for patients newly diagnosed as having bipolar disorder. In these cases, both the dosage of lithium and the dosage of choline will have to be established. The preferred procedure is to begin by optimizing the dosage of lithium using standard procedures, well known in the art (Bloom, F. and Kupfer, D., *Psycopharmacology. The Fourth Generation of Progress*, Raven Press (1994)), and to then administer choline as set forth above. Alternatively, an optimal combined dosage may be determined by using a fixed ratio of lithium to choline and adjusting the daily dosage of the agents together. Typically the weight ratio of the combined medication should be about 3 to 10 units of choline for each unit of lithium.

C. Treatment of Patients Taking Thyroid Medication

A special problem is presented by patients taking high doses of thyroid medications such as thyroxine (see cases 5 and 6 under "Example 2"). These medications appear to block both the increases in brain choline levels associated with choline administration as well as the beneficial effects of choline on mood stabilization. Since clinical or subclinical hypothyroidism is one of the major factors associated with some forms of bipolar disorder (Roy-Byrne et al., *Br. J. Psychiatry* 145:543–550 (1984)), and since high doses of thyroid medications are sometimes prescribed as a therapy for patients with rapid cycling bipolar disorder, this observation is of considerable importance. Low or usual doses of thyroid medication may be used without blocking the action of choline.

Improvement in brain choline uptake and mood stabilization can be obtained if thyroxine is gradually reduced while maintaining an elevated (at least 50 mg/kg/day) dosage of choline. As demonstrated by case 6 below, it may sometimes be possible to completely eliminate thyroxine without adversely affecting the patient.

D. Compositions Comprising Lithium and Choline

The biochemical form of lithium is not critical to the invention. Although it is expected and preferred that most patients receive lithium carbonate, lithium should have the same therapeutic effect regardless of its source. Other salt forms that could serve as a source of lithium include: lithium benzoate, lithium bromide, lithium cacodylate, lithium caffeine sulfonate, lithium chloride, lithium citrate, lithium dithiosalicylate, lithium formate, lithium glycerophosphate, lithium iodate and lithium salicylate. The lithium salts may be given in a substantially pure form or mixed with other compounds, foods, or therapeutic agents as the exigencies of individual cases require.

It is preferred that choline be administered to patients in the form of a salt, the most preferred being choline bitartrate. Other salts that can be used include choline chloride, choline dihydrogen citrate, choline salicylate and choline magnesium trisalicylate. These salts may be administered either individually or in various combinations in order to provide the desired amount of free choline. Because of difficulties in accurately predicting dosage, complex dietary precursors of choline such as phospholipids should not be used as the sole or primary source of therapeutic choline. For example, the invention does not encompass methods or compositions which use lecithin as the sole or primary source of choline. This phospholipid is a major component of cellular membranes and its administration in high doses may have undesirable effects on membrane structure and permeability. In addition, very high doses of lecithin, i.e. 15–30 grams per day, would tend to promote cardiovascular disease (Robbins, et al., *Pathologic Basis of Disease, 3rd Edition*, W. B. Saunders Co., Philadelphia (1984)).

Choline may be administered using currently available preparations, or in any pharmaceutically acceptable vehicle. It can be provided in dosage forms such as tablets, capsules, powder packets, or liquid solutions for oral administration. Methods for preparing these dosage forms are well known in the art (see e.g., *Remington's Pharmaceutical Sciences*, 16th Ed., A. Oslo Ed. Mack, Easton, Pa. (1980)). When given orally, therapeutically inert agents may be added to improve the palatability of choline or additional therapeutic agents may be added. It will be appreciated that one desirable composition is one which includes both lithium and choline. Preferably, on a weight basis, this composition has 3–10 units of choline per unit of lithium by weight. The amount of lithium in such a composition can be chosen for convenience of administration and is preferably between 50 mg and 1000 mg.

Individual preparations of choline and lithium may also be provided in the form of a kit, comprising a carrier (e.g. a box or bag) compartmentalized to receive one or more components (bottles, vials, packets etc.) in close confinement. It is expected that such a kit would be carried by patients with bipolar disorder and that it would contain written instructions concerning the way in which the enclosed drugs should be taken, potential side effects etc. The kit should be portable, and be generally convenient for use by patients.

At least one of the components of the kit should contain the source of lithium and, at least one, the source of choline to be administered to the patient with bipolar disorder. It is preferred that the source of choline be a choline salt, most preferably choline bitartrate. Containers with agents other than either choline or lithium may also be provided. The container with the lithium source and the container with the choline source should have sufficient material to provide for at least one complete dosage. For example, if a patient is supposed to take lithium and choline three times a day, the kit should contain at least one third of the total daily dosage of each agent.

For parenteral administration, preparations containing one or more biochemical forms of choline may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

E. General Considerations Concerning the Combination of Lithium and Choline in Treating Bipolar Disorder As indicated by the data presented below, the extreme mood fluctuations of patients with bipolar disorder can be ameliorated through the administration of choline in combination with lithium. These agents work together to produce an overall effect which neither agent can achieve alone. Based upon observations of the inventors, a number of aspects of the present invention may be described in greater detail.

The majority of patients with bipolar disorder who are treated with the methods and compositions of the present invention, i.e. patients treated with a combination of choline and lithium, will exhibit a reduction in the number and severity of manic episodes associated with this illness. The effect of the therapy on depressive symptoms is likely to be somewhat more variable. It is expected that some patients will experience continued, intermittent depression following treatment whereas others will experience a resolution of depressive symptoms. The effects of choline on mania should appear earlier and be more robust than the effects on depression. In addition, for those patients who respond, the mood-stabilizing effects of choline should be accompanied by a rise in the basal ganglia choline resonance, as determined by $^1$H-MRS. These neurochemical findings are consistent with one of the main hypotheses underlying this invention—continuous oral administration of choline in the presence of ongoing lithium will produce a rise in the brain choline resonance in humans ("choline trapping").

In some instances, the patients treated with the present methods and compositions may not initially respond well to the therapy. One reason for the lack of response may be that the patient is concurrently taking a thyroid medication such as thyroxine. In these cases, it may be possible to obtain the desired result by gradually eliminating the thyroid medication while maintaining the administration of choline and lithium.

Several reports describing the relationship between choline transport and thyroid status in animal models have been published. In each study, increasing thyroid activity was associated with a diminished concentration of choline in the brain (Toide et al., *Eur. J. Pharmacol.* 233:21–28 (1993); Cornatzer et al., *Int. J. Biochem.* 16:567–570 (1984)). Although it is unclear whether these animal data can be extrapolated to humans, the results are largely consistent with the observed negative effect of thyroid medications on the treatment of bipolar disorder using the methods and compositions of the present invention.

The Examples below are for illustrative purposes only and are not intended to limit the scope of the invention.

EXAMPLES

EXAMPLE 1

Elevation of Brain Choline Levels After the Administration of Oral Choline

In this study, choline-containing compounds in human brain (principally phosphocholine, glycero-phosphocholine, and choline) were measured by $^1$H-magnetic resonance spectroscopy, before and after the ingestion of 50 mg/kg choline in four normal control subjects. Substantial and remarkably similar increases in the brain choline resonance occurred in each subject, with a nearly two-fold rise in the choline resonance observed 3 hr following choline ingestion (p=0.008 versus baseline). One subject also received a dose of 200 mg/kg choline, and exhibited a proportionally larger increase in the brain choline resonance.

A. Methods

Subjects and Choline Ingestion Protocol

All four subjects were psychiatrists without a personal history of psychiatric disorders or major medical problems. After giving written informed consent, subjects underwent an initial $^1$H-MRS session to determine the intensity of the baseline brain choline resonance signal, and blood was drawn for the determination of baseline plasma choline concentration. Immediately following these procedures, the subjects ingested the equivalent of 50 mg/kg of free choline in capsules of choline bitartrate, with 400 ml of apple juice. Subjects then underwent repeat $^1$H-MRS and bloodwork 1.25 and 3.0 hr following the choline ingestion. One subject also ingested 200 mg/kg of free choline in a separate session, and underwent $^1$H-MRS at various timepoints over the subsequent 24 hr.

Magnetic Resonance Spectroscopy

Human brain choline resonance was determined by $^1$H-MRS, using a 1.5 T General Electric Magnetic Resonance Imaging device. An 8 cm$^3$ voxel centered on the head of the caudate and the putamen was determined from coronal, $T_1$-weighted, 6 mm contiguous scout images. Scout images were performed for each MRS session to ensure correct voxel localization. Voxel was 20 mm×20 mm×20 mm, centered on the head of the caudate nucleus and putamen. In order to minimize possible repositioning effects (e.g., partial volume errors), in each case the anterior edge of the voxel corresponded to the anterior margin of the caudate nucleus.

The basal ganglia was Chosen as the region to study due to its rich innervation with cholinergic neurons, high levels of choline metabolites in animal studies (Millington, W. R., et al., *J. Neurochem.* 38:1748–1752), as well as other MRS research in the literature examining this brain area in patients with mood disorders (Charles, H. C., et al., *Biol. Psychiatry* 31:99A). A modified stimulated echo acquisition mode (STEAM) pulse sequence was used to acquire the $^1$H MR spectra using a TR=2 sec, TE=30 msec, 1024 data points, and 800 Hz spectral width (Griffey, R. H., et al., *J. Magn. Reson.* 88:161–166). The total data acquisition time was just over 13 min as 400 transients were averaged. Raw data was transferred to a Sparc2 workstation (Sun Microsystems, Mountain View, Calif.) and analysis was performed using SA/GE software (General Electric Medical Systems, Milwaukee, Wis.). The FID is zero-filled to 2048 data points and processed with an experimental filter, resulting in line broadening of 1 Hz after Fourier transformation. A spline function was used to correct the baseline for residual water signal. Following manual phase correction, the choline, creatine/phosphocreatine, and N-acetylaspartate resonance lines were fit to Gaussian line shapes using an iterative Marquardt algorithm.

Three major resonance signals were examined: Choline (Cho), Creatine (Cr), and N-acetyl aspartate (NAA). The Cr resonance is composed of creatine and phosphocreatine, and is often used as an internal standard, because this signal appears to be stable over time and across a range of physiological states. Thus, relative concentrations of Cho and NAA were determined using the ratios of the Cho or NAA resonance intensities to the Cr resonance intensity. This method to calculate relative concentrations allows comparisons across subjects. To determine the reliability of this method, one normal volunteer underwent repeated $^1$H MRS studies on four occasions over a 6-month period. The mean (±SD) $^1$H-MRS results for Cho/Cr was 0.43±0.04, and that for NAA/Cr was 0.94±0.15.

Plasma Choline Determination

Plasma choline was determined by high-performance liquid chromatography (HPLC) coupled to electrochemical detection (Klein, J., et al., *J. Neurochem.* 58:870–876; Marshall, D. L., et al., *Brain Res.* 629:269–274). Blood was drawn into heparinized tubes, centrifuged, and was stored at −70° C. For the analysis of choline, 100 µl of plasma was added to 500 µl of ice-cold methanol in a polypropylene tube, and centrifuged at 4° C. for 15 minutes at 15,000 rpm to precipitate the proteins. The protein pellet was discarded and all of the supernatant (approximately 400 µl) was placed in a separate tube, to which was added 240 µl of water and 640 µl of chloroform. The mixture was vortexed for 10 sec and then centrifuged for 5 min at 4000 rpm. All of the upper/aqueous phase (approximately 500 µl) was placed in a fresh tube and dried to a powder using a vacuum concentrator. To remove any protein residue, the samples underwent a third extraction in methanol:water:chloroform (1:1:2). The dried power was then reconstituted and analyzed for choline.

Choline was determined by HPLC (Waters, Model 710B) with a choline oxidase column coupled to an electrochemical detector. The mobile phase (flow rate 1.2 ml/min) contained 50 mmol/L $Na_2HPO_4$, and 0.005% Kathon, at a pH of 8.5. Choline was enzymatically converted to hydrogen peroxide, which was measured electrochemically on a platinum electrode at +300 mV (versus a palladium reference electrode).

B. Results

Substantial and remarkably similar increases in the brain choline resonance occurred in each subject 3 hr after the ingestion of 50 mg/kg free choline (FIG. 1). The increase (compared to baseline) in the mean (±SD) brain Cho:Cr resonance signal for all four subjects was 7.7±15.1% at 1.25 hr (p=ns; Kruskal-Wallis), and 94.2±35.5% at 3.0 hr (p=0.008); Kruskal-Wallis; FIG. 1).

In a separate experiment, one subject also received 200 mg/kg free choline. At this higher dose, proportionally larger peak increases in the choline resonance intensity occurred at 1.5 and 4 hr after choline ingestion (Cho:Cr=0.97; 110.9% increase and Cho: Cr=1.24; 169.6% increase, respectively). This one subject was studied three times over an 8 hr period and then at 24 hr after choline ingestion. His brain choline resonance remained elevated at 8 hr (Cho:Cr=0.70; 52.2% increase), but returned to baseline values by 24 hr (Cho:Cr= 0.43, 6.5% decrease). No changes in NAA/Cr were observed at any time following either dose of oral choline.

Plasma choline rose significantly as well. Following 50 mg/kg oral choline, the mean (±SD) rise in plasma choline for the subjects was 54.9±23.9% at 1.25 hr, and 100.3±60.1% at 3.0 hr (p=0.01; Kruskal-Wallis). There was no significant correlation between serum and brain choline measures (n=4, t=0.33; p=0.5; Kendall's rank correlation).

No serious adverse reactions to 50 mg/kg oral choline occurred. One subject experienced low mood and anergia on the day following the choline ingestion, which remitted within 18–24 hr. One other subject experienced an episode of mild diarrhea. The subject who received 200 mg/kg oral choline experienced moderately severe diarrhea for several hours. No overt chances in mood or cognition were noted in this subject

EXAMPLE 2

Clinical Studies

A summary of the clinical results that have been obtained to date in examining the effect of choline and lithium on bipolar disorder is shown in Table 1. A detailed description of methodology and of the results obtained for 6 patients is set forth below.

A. Methods

Patients

Six treatment-refractory rapid-cycling bipolar patients were offered open treatment with oral choline bitartrate, in addition to lithium and other ongoing treatments. The determination of the clinical response to choline treatment was made blind to the $^1$H-MRS findings. The individual case histories are described below.

Mood ratings

Consistent with our routine clinical practice, all patients were instructed to complete mood charts on which the best and worst mood state for each day is rated on a 7-point scale. Patients could rate their mood as normal, depressed (mild, moderate, or severe), or manic (mild, moderate, or severe). Mood charts were maintained by 4 of the 6 patients; 2 patients refused to comply with daily mood charting. For the period before and after choline administration, all 6 patients were repeatedly evaluated with a structured clinical interview based on the major depression and mania sections of the Structured Clinical Interview for DSM-III-R Diagnosis American Psychiatric Association et al., *Diagnostic and Statistical Manual of Mental Disorders*, Third Edition-Revised (1987)

Choline administration

Treatment was initiated with 6–12 capsules of 780 mg choline bitartrate (Solgar Vitamin Co., Inc., Lynnbrook, N.Y.; each supplying the equivalent of 350 mg of free choline), in a split BID dosage schedule. By the end of the first week, the choline dosage was typically increased to 3–8 g per day of free choline, as a maintenance dosage, also given in divided dosages. This dosage range for choline was chosen based on recent work indicating that 50 mg/kg/day produces a substantial rise in the brain choline resonance signal (see Example 1; and Stoll et al., *Biol. Psychiatry* 37:170–174 (1995)).

Magnetic Resonance Spectroscopy

The human brain choline resonance was determined by $^1$H-MRS, using a standardized method described in detail elsewhere (see Example 1; and Stoll et al., *Biol. Psychiatry* 37:170–174 (1995)). Five of 6 patients underwent at least 2 $^1$H-MRS scans: One before receiving choline and at least I during, choline treatment. The basal ganglia was chosen as the region to study due to its rich innervation with cholinergic neurons, high levels of choline metabolites in animal studies (Millington et al., *J. Neurochem.* 38:1748–1752 (1982), and the results of MRS research which suggest abnormalities in the level of choline-containing compounds in this brain area in patients with mood disorders (Charles et al., *Biol. Psychiatry* 31:99A (1992); Renshaw et al., *Abstracts of the Society of Biological Psychiatry Annual Meeting* (1994)). Two major resonance signals were examined: choline (Cho) and creatine (Cr). The Cr resonance is composed of creatine and phosphocreatine, and was used as an internal standard. Thus, the relative concentration of choline-containing compounds was determined using the ratio of the Cho resonance intensity to the Cr resonance intensity. This method for calculating relative Cho concentrations facilitates comparisons across subjects.

B. Results

Case 1: Mr. A is a 49 year-old single, white man with a 30-year history of dysphoric mood symptoms. Initial drug treatments for apparent depressive symptoms were maprotiline (up to 225 mg per day), and fluoxetine, both without effect. Three years following the fluoxetine trial, he began to experience daily mood swings. A diagnosis of rapid-cycling bipolar disorder was made and lithium was prescribed, which was helpful for about 1 year. Due to the recurrence of depressive symptoms, tranylcypromine was added to the lithium. However, after 5 months of increasing doses of tranylcypromine in combination with lithium, the patient developed extreme irritability and spending sprees, mixed with intense dysphoria, and brief periods of persecutory delusions and auditory hallucinations. He presented to the Massachusetts General Hospital Bipolar Clinic 6 months later, complaining of dysphoria. Mood charting over the next month, revealed mood cycles with a periodicity of 2–3 days. As tranylcypromine was gradually discontinued, his cycle frequency slowly lengthened to 15 days. A 15-week valproate trial (serum level of 101 mg/L) in combination with lithium (serum level of 1.1 mEq/L) was not helpful. Laboratory studies, including TSH were within normal limits.

Figure 2:
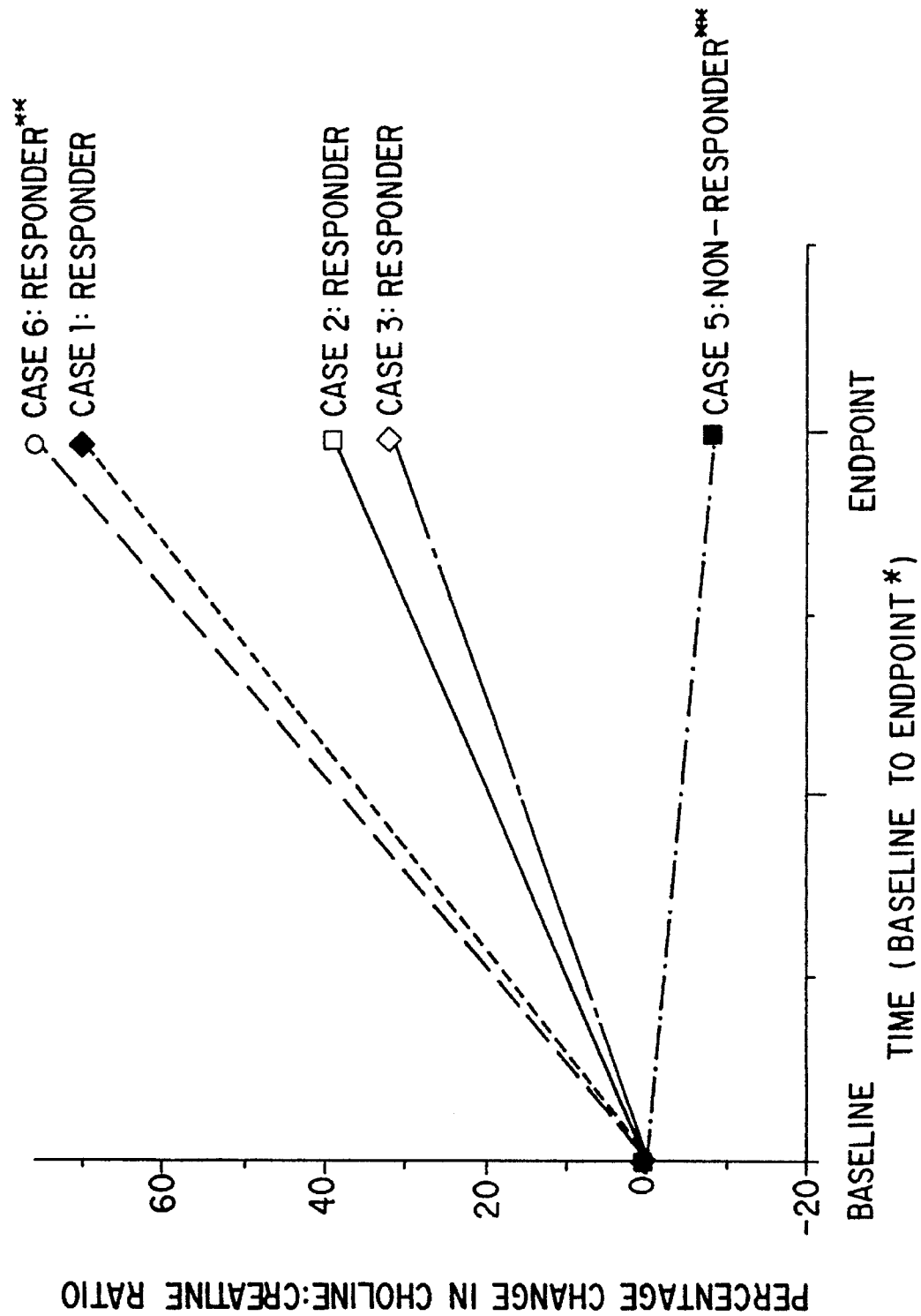
FIG. 2.

After obtaining MRS for determination of his baseline basal ganglia choline resonance, treatment with choline began at the equivalent of 4000 mg per day of free choline. Choline was increased to 6000 mg per day after 1 week, because of ongoing symptoms, including insomnia. In the month prior to choline, his mood chart revealed 10 of 62 ratings in the manic range, 32 of 62 ratings in the depressed range, and 20 normal ratings (FIG. 2). By the second month of choline therapy, of 60 ratings, none were in the manic range, 5 ratings indicated mild depression, and 55 ratings were normal (FIG. 2).

Before choline treatment, the choline to creatine resonance ratio in his basal ganglia was 0.63. This increased to 0.83 (31.7% increase) following one week of choline administration (FIG. 1).

Case 2: Mr. B is a 36 year-old married, white man, with bipolar disorder, panic disorder with agoraphobia, and a past history of alcohol abuse. In the preceding year, he had 2 complete biphasic mood episodes. These mood cycles manifested as 7–10 days of mania, followed by a depressive episode which lasted 4–6 months. Lithium, 1200 mg per day, clonazepam 0.75 mg per day, and several trials of antidepressants, including desipramine were ineffective. Fluoxetine and paroxetine caused ataxia and tremor, and venlafaxine led to a recurrence of severe panic.

Figure 3:
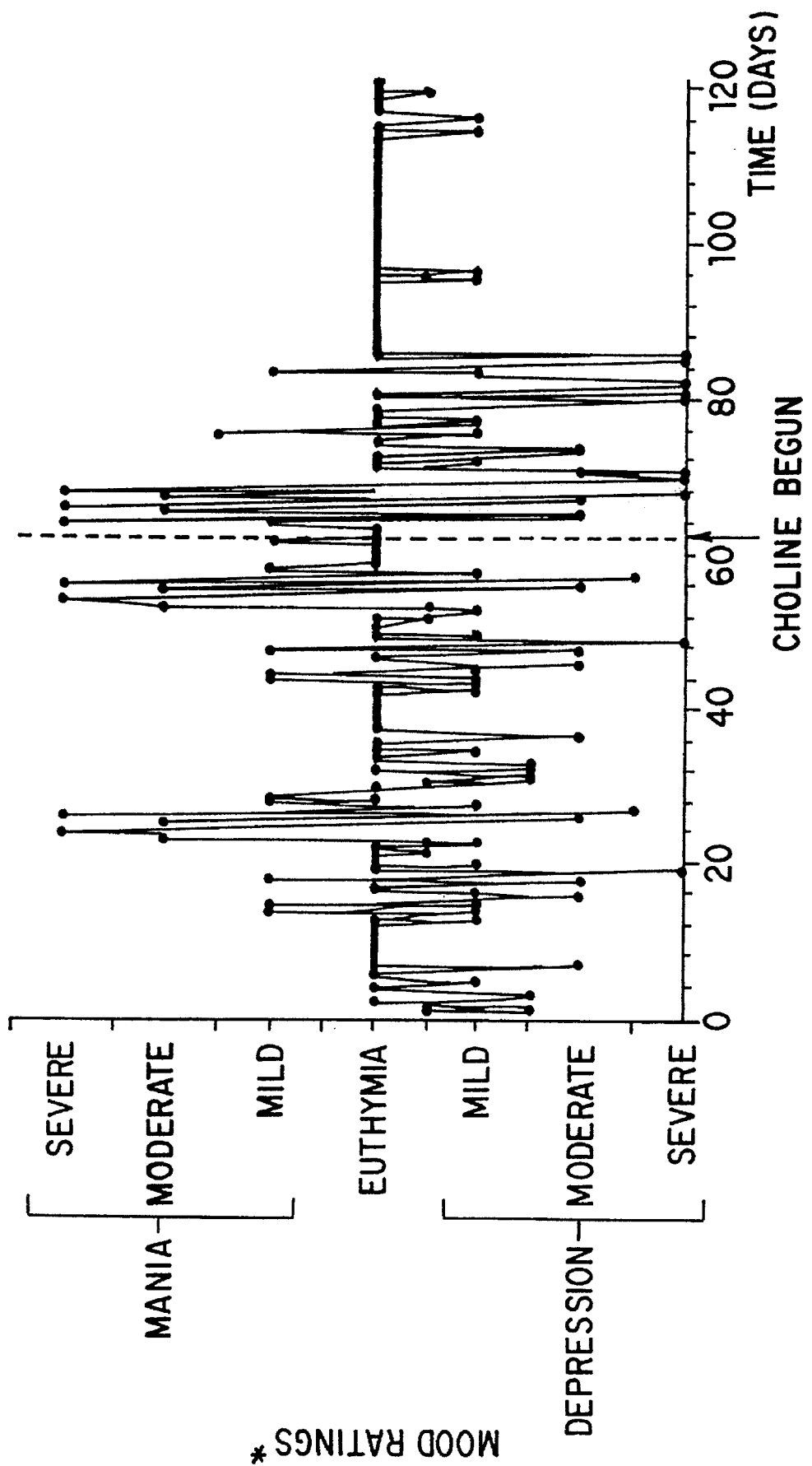
FIGS. 3–6.

In the month prior to choline, his mood charting revealed persistent and severe depressive symptoms, frequently alternating with mild mania, even within the same day (FIG. 3). Choline bitartrate was added to the ongoing lithium and clonazepam treatment, beginning at the equivalent of 1000 mg BID of free choline, and increasing to 1000 mg T.I.D. after 3 days. After 4 days of choline therapy, he had a complete remission of depressive symptoms, and no abnormal mood elevation (FIG. 3). He has remained euthymic for 16 weeks and denies any adverse reactions to choline treatment.

MR spectroscopy was not performed.

Case 3: Ms. C is a 30 year-old single, white woman referred to our center for treatment-resistant rapid-cycling bipolar disorder. The patient had the onset of mania at age 19, and had been rapidly-cycling, for 2 years prior to our evaluation. This was apparently precipitated by a brief trial of clomipramine. The patient also carried diagnoses of anorexia nervosa and possible borderline personality disorder. Trials of neuroleptic drugs (chlorpromazine, haloperidol, perphenazine, and thiothixine) in various combinations with lithium, carbamazepine, valproate, and clonazepam were only partially helpful in controlling her rapid-cycling symptoms.

At the time of referral to our center, she was receiving haloperidol 6 mg per day, lorazepam 2 mg per day, lithium carbonate 900 mg per day, and carbamazepine 600 mg per day. Her laboratory studies, including TSH were all within normal limits. She had recently lost her job as a nurse due to bizarre behavior. The initial treatment recommendation was to maximize her lithium therapy. However, despite a lithium level of 1.2 mEq/L, she continued to exhibit alternating cycles of mania and depression, each lasting 1–3 weeks, for about 9 months. Her referring psychiatrist restarted phenelzine, which increased the cycle frequency, resulting in hospitalization for a severe manic episode.

Following hospital discharge, the patient returned to our center, and underwent MR spectroscopy for determination of her baseline brain choline level. She agreed to a trial of choline bitartrate to treat her rapid-cycling, symptoms, and received the equivalent of 1800 mg of free choline T.I.D., as well as continued lithium 900 mg per day, thiothixine 5 mg per day, and triazolam 0.125 mg qhs. After 7 days, the choline was increased the equivalent of 1800 mg QID of free choline.

Figure 4:
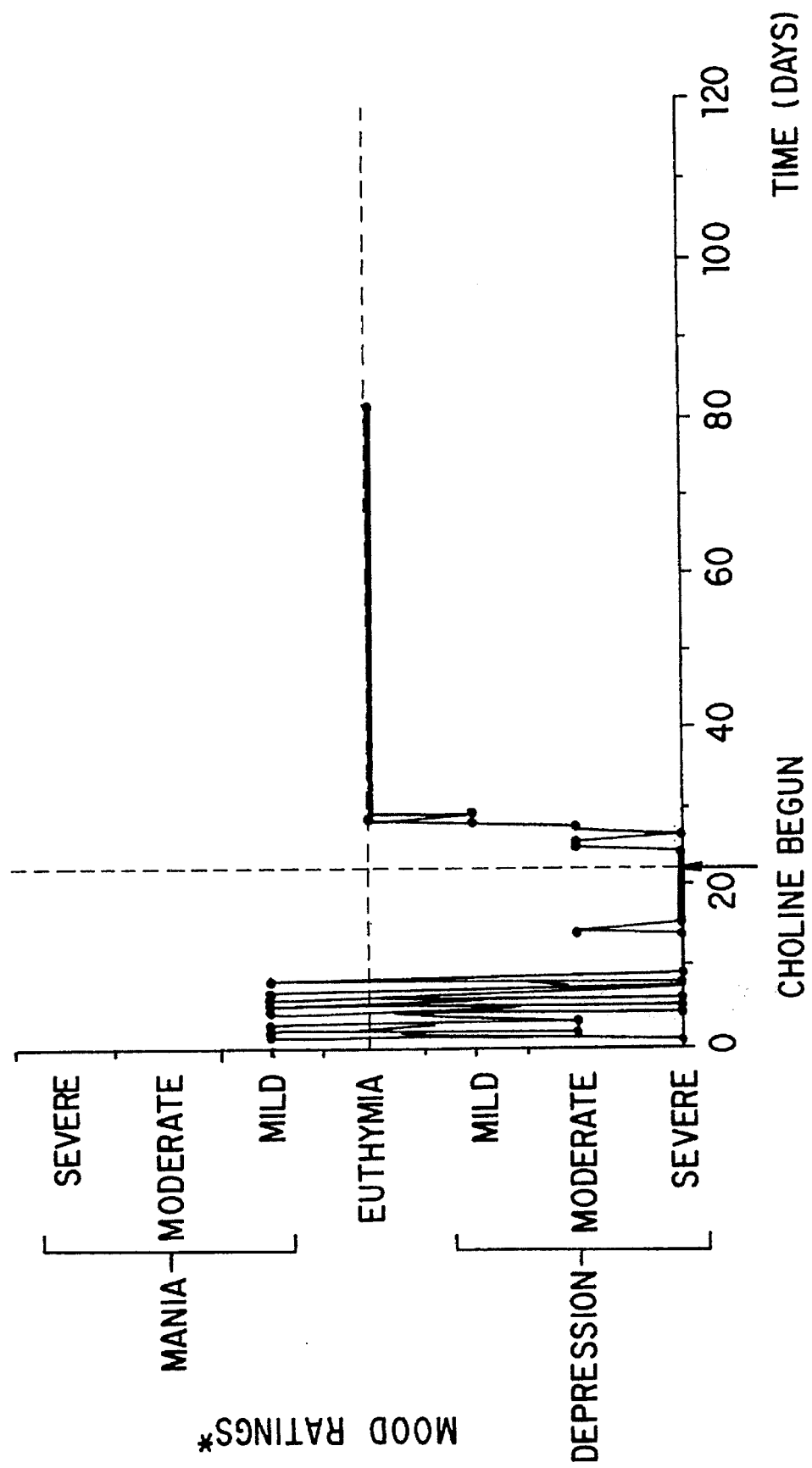

In the 1 month prior to choline administration, only 6 of her 62 mood chart ratings were within the normal range (20 depressed ratings and 36 mania ratings; FIG. 4). In the month following choline, 23 of 60 ratings were within the normal range, 31 ratings were in the depressed range and 6 revealed mania (FIG. 4). Due to continued dysphoria, the referring psychiatrist discontinued choline and restarted phenelzine. Within 10 days, the patient was admitted for another manic episode, and has not been seen for follow-up in our center.

On MRS, the patient exhibited approximately a 50% increase in the choline to creatine resonance ratio in her basal ganglia (from 0.662 to 0.920) after one week of choline administration (FIG. 1).

Case 4: Mr. D is a 33 year-old, white, male lawyer with a history of probable cyclothymia, beginning at age 15. His first clear manic episode occurred at age 23, and required a leave of absence from law school. Despite this and multiple other episodes, he received no treatment for many years. He worked excessive hours, and on the day he moved into his new home, he started remodeling his house, but never finished this and many other projects. He had problems with overspending, sexual indiscretions and extremely poor judgment.

The patient was referred to our center during the last year of law school, and lithium was started. Prior to lithium, the patient reported 3–5 mood cycles per week for many years. Following, lithium 1800 mg per day (level up to 1.4 mEq/L), clonazepam 1 mg per day, and propanolol for tremor, he continued to experience approximately 2–3 mood cycles per week. Valproate, in combination with lithium, was not tolerated due to severe diarrhea. He would not keep a mood diary, so his progress was based on frequent prospective clinical assessments.

Choline bitartrate was introduced at the equivalent of 4600 mg of free choline, in a single AM dose on an empty stomach. The single dose was due to his unwillingness to take medication while at work. At a choline dosage of 6000 mg per day (free choline), his colleagues noted a fishy odor on his breath. The fishy odor resolved after the dosage was reduced to 5000 mg, per day of free choline. The patient reported improved mood stability by the end of the first week, and his mood completely normalized by 10 days. Over the next 3 months, he had one day of feeling, slightly "giddy", and one day several weeks later, where he was slightly depressed. Due to mild diarrhea and abdominal discomfort, the choline was reduced to 3000 mg per day, and he has maintained his improvement. The patient was able to complete law school, reestablish a relationship with the mother of his child and function more reliably in a parental role.

The patient underwent MRS, and the choline to creatine resonance ratio in his basal ganglia was found to increase from 1.02 prior to choline to 1.73 (69.6% increase) following one week of choline administration (FIG. 1).

Case 5: Ms. E is a 55 year-old, white, married mother of 3 children. She had a long, history of psychiatric difficulties and migraine headaches dating back to childhood. She was admitted at age 22 for a postpartum depression. At her second psychiatric hospitalization, 15 years later, she presented with acute mania and thyroid cancer was also diagnosed. She underwent a total thyroidectomy, and has been maintained on 0.3–0.4 mg per day of thyroxine since that time. For 14 years, she had 4–6 mood episodes per year (mania, mixed mania, and depression), but largely refused treatment. She has been unable to tolerate therapeutic levels of lithium, valproate, and carbamazepine. However, she has continued lithium, 300 mg per day for many years because, upon complete discontinuation of lithium, she suffers the abrupt onset of depression and/or mania.

Choline was begun at 1000 mg BID of free choline, which was increased to 2000 mg BID after 1 week. The patient stopped the choline after 6 weeks due to lack of improvement. She refused to keep a mood chart. The ratio of her brain resonance intensities of choline/creatine declined from 0.81 prior to choline, to 0.66 (18.5% decrease) at 1 week of choline therapy, to 0.46 (43.2% decrease from baseline) at week 3. Following a brief switch to hypomania, and an increase in lithium to 600 mg per day during week 4 of choline, her brain choline/creatine ratio rose to her baseline value of 0.81. Intolerable tremor and slurred speech led to a decrease in lithium to 300 mg per day during week 6 of choline. Repeat MRS, two weeks after lithium was lowered back to 300 mg per day, revealed that her brain choline/creatine dropped to 0.68 (16% decline; FIG. 1). She has subsequently responded well to paroxetine. There were no gastrointestinal or other side-effects to choline (tremor and slurred speech had occurred on all prior attempts to increase her lithium).

Case 6: Mr. F is a 35 year-old, white physician with a history of mood and somatic symptoms since age 5. At age 18, he was treated for an overdose of chlordiazepoxide, which he reports was not a suicide attempt, but an effort to control "overwhelming, feelings of agitation." Despite the chronic and recurrent nature of his symptoms, his high intelligence and periods of exceptional productivity enabled him to gain entrance into medical school. During medical school he continued to experience dysphoric mood episodes and was referred for psychiatric treatment during a major depressive episode. After 2 weeks of treatment with fluoxetine, he experienced his first full manic episode, which resulted in a 6-week psychiatric hospitalization.

Over the next 7 years, he continued to suffer dozens of mood episodes each year, despite trials of more than 50 medications. His mood episodes typically consisted of an initial phase of depression lasting 3–7 days, followed by 1–2 days of extreme irritability during which his temper was violent. He was referred to a bipolar disorder specialty clinic, where hypermetabolic thyroid supplementation was recommended. He reported improvement with thyroxine 0.4 mg per day, added to his ongoing regimen of lithium (serum level 1.2 mEq/L), carbamazepine (serum level 9.2 ng/ml), and thioridazine (50–100 mg per day). On evaluation in our center, mood charting, confirmed the patient's report that while receiving hypermetabolic thyroid supplementation he was experiencing 2–4 mood cycles per month. His medical record from previous treaters documented clear worsening on 2 attempts to lower his dose of thyroxine.

The patient developed cognitive impairment, but no apparent benefit from increasing dosages of lithium and carbamazepine. Additional trials of clonidine, propanolol, valproate, and risperidone were unsuccessful. The patient then underwent an MRS study to determine his brain choline resonance intensity prior to starting choline. His daily mood chart in the month preceding choline revealed no ratings in the normal range. The patient received 4 weeks of choline bitartrate at the equivalent of 6000 mg per day of free choline. However, there was no improvement in his mood symptoms. Repeat MRS at 2 weeks of choline treatment revealed no change in his brain choline resonance.

Figure 5:
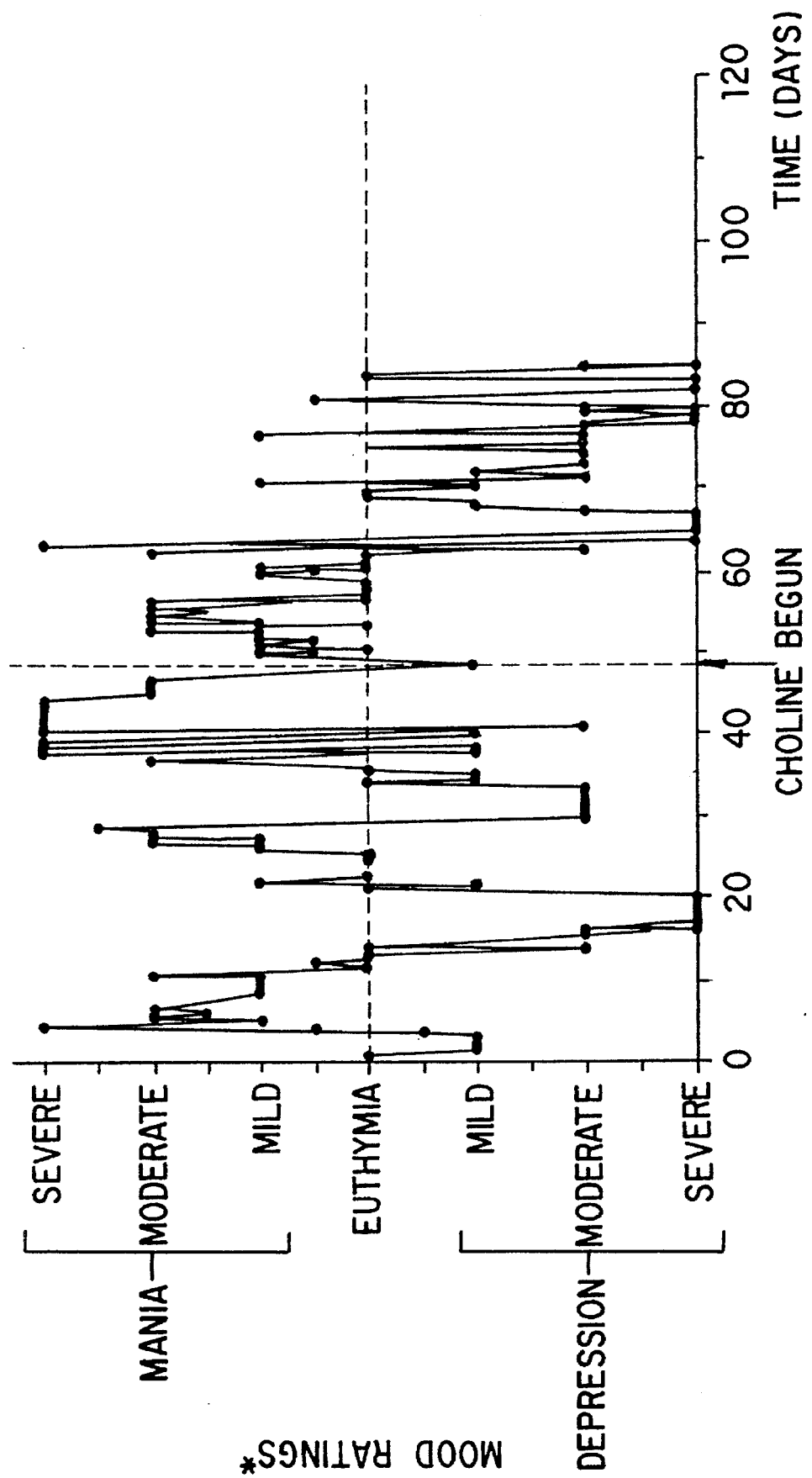
Figure 6:
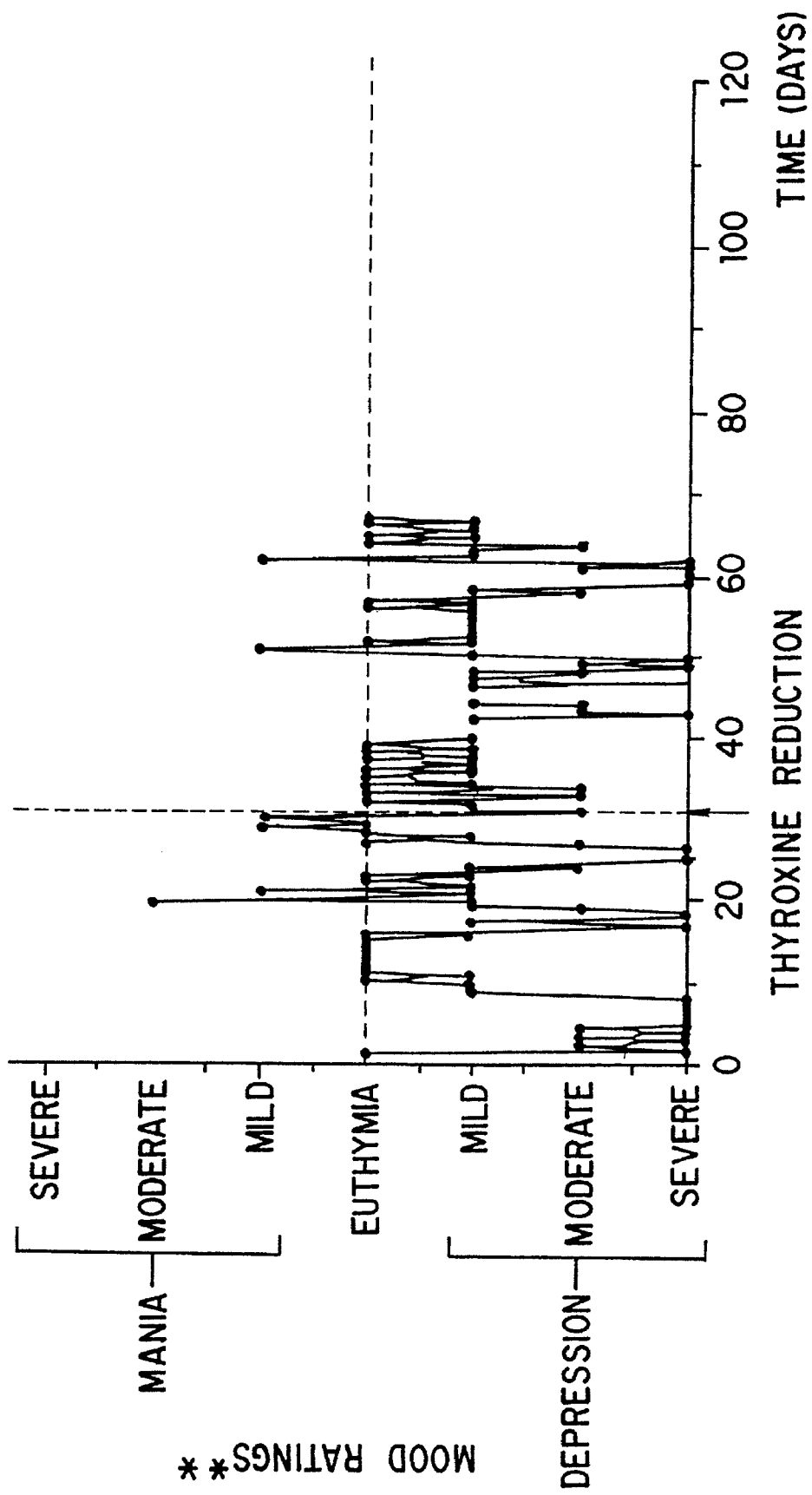

This patient was similar to case 5 in several ways. The failure of choline to improve mood symptoms was accompanied by lack of increase in the brain choline resonance and with high-dose thyroid hormone treatment. Based on these possible associations, Mr. F's choline, lithium, and carbamazepine were continued, and his thyroxine was reduced to 0.3 mg per day. After 2 weeks, a significant improvement occurred and his thyroxine was further reduced to 0.2 mg per day. On his mood chart during the subsequent month, only 1 brief period of moderate dysphoria was evident, with some persistent mild depressive symptoms (FIG. 5). The following month, his thyroxine was gradually discontinued, and he has continued to experience a substantial remission of mood symptoms. His mood charting reveals few or no manic symptoms, but persistent intermittent mild to moderate depressive symptoms, which he finds tolerable.

Repeat MRS approximately 6 weeks after discontinuing his thyroxine while continuing choline treatment revealed a marked rise in his choline: creatine resonance ratio from a baseline value of 0.75 to 1.32, an increase of more than 75% (FIG. 1).

All references cited herein are fully incorporated by reference. Having now fully described the invention, it will be understood by those of skill in the an that the invention may be performed within a wide and equivalent range of conditions, parameters and the like, without affecting the spirit or scope of the invention or any embodiment thereof.

TABLE 1

Choline & Lithium Interactions in Bipolar Disorder: Summary of Clinical Results

| # | ID | Age | Sex | Diagnosis | Past Failed Trials | Choline dose/duration | Concurrent Meds | Response to Choline | Comments |
|---|---|---|---|---|---|---|---|---|---|
| 1 | CB | 49 | M | Rapid-cycling MDI | lithium, VPA maprotiline tranylcypromine fluoxetine | 6 g/d 26 weeks | lithium | +++ | Marked response to choline therapy |
| 2 | FD | 55 | F | Rapid-cycling MDI | lithium CBZ, VPA (intol) fluoxetine, SSRIs | 4 g/d 6 weeks | lithium (low-dose) thyoxine (0.4 mg/d) | 0 | subsequent response to paroxetine |
| 3 | GK | 35 | M | Rapid-cycling MDI | lithium, CBZ, VPA risperidone | 6 g/d 14 weeks | lithium thyroxine taper | ++ | Good response to choline only after high-dose thyroxine discontinued |
| 4 | MS | 36 | M | Rapid-cycling MDI Panic disorder | lithium, clonazepam SSRIs, DMI, venlafaxine | 3 g/d 28 weeks | lithium clonazepam | +++ | till remission of symptoms within 4 days of starting choline |
| 5 | DM | 30 | F | Rapid-cycling MDI Anorexia nervosa Axis 2 | clomipramine (mania) neuroleptics lithium, CBZ, VPA clonazepam | 7 g/d 5 weeks | lithium thiothixine triazolam | ++ | Good anti-manic response to choline, but depression/dysphoria persisted or worsened |
| 6 | JR | 33 | M | Rapid-cycling MDI | lithium VPA (intol) clonazepam | 5 g/d 22 weeks | lithium clonazepam | +++ | Marked improvement in mood. Fishy body odor at 6 g/d resolved at 5 g/d of choline |
| 7 | KG | 31 | F | Rapid-cycling MDI Bulimia Axis 2 | lithium alone CBZ, VPA (intol) SSRIs | 4 g/d 3 weeks | lithium amoxapine | ++ | less irritable & hypomania |
| 8 | EJ | 30 | F | MDI-depressed Axis 2 SLE | bupropion paroxetine ECT (memory loss) | 4 g/d 5 weeks | lithium, VPA ECT | +/− | subjectively less memory loss with ECT. Has elected to stay on choline |
| 9 | AM | 35 | F | Rapid-cycling MDI (refractory depression) | lithium, VPA CBZ, risperidone SSRI, felbamate | 5 g/d 8 weeks | lithium venlafaxine zolpidem | + | less depressed less impulsive relapse when choline briefly stopped |
| 10 | BO | 58 | F | MDI-mixed | lithium amoxapine bupropion | 2 g/d 12 weeks | amoxapine | + | remains mildly depressed, but "best" she's ever felt |
| 11 | LS | 34 | F | Rapid-cycling MDI | lithium multiple antidepressants | 2 doses only 5 g/d 20 weeks | paroxetine | + | too inconvenient less depressed no switch to mania |
| 12 | LS | 38 | M | h/o Rapid-cycling now chronically depressed | | | | | |
| 13 | PW | 28 | F | Rapid-cycling MDI MDI PTSD asthma | lithium desipramine (mania) | 1 dose only 2–4 g/d 8 weeks | bupropion lithium clonazepam | + | too inconvenient hypomania on bupropion reduced following choline |
| 14 | MB | 31 | F | | | | | | |
| 15 | JS | 52 | M | MDI | tranylcypromine (mania, cycling) | 4 g/d 4 weeks | tranylcypromine | ++ | choline reduced insomnia appeared to prevent cycling |

TABLE 1-continued

Choline & Lithium Interactions in Bipolar Disorder: Summary of Clinical Results

| # | ID | Age | Sex | Diagnosis | Past Failed Trials | Choline dose/duration | Concurrent Meds | Response to Choline | Comments |
|---|----|-----|-----|-----------|--------------------|-----------------------|-----------------|---------------------|----------|
| 16 | RH | 36 | M | Rapid-cycling MDI Narcolepsy, ADHD | lithium, VPA, CBZ, clonazepam, neuroleptics | 4 g/d 12 weeks | lithium risperidone | +++ | Choline has been the only drug able to reduce his cycling |
| 17 | JW | 44 | F | Rapid-cycling MDI | lithium, VPA, CBZ | 3.5 g/d | lithium VPA | + | Choline eliminated recurrent hypomanias, but did not reduce recurrent depression |
| 18 | PG | 29 | M | Rapid-cycling MDI Axis 2 hiatal hernia | lithium, CBZ, VPA, neuroleptics, DMI | 2 doses only | | | Choline led to a worsening of dyspepsia in this patient with chronic nausea and dyspepsia |

What is claimed is:

1. A method for treating bipolar disorder in a patient comprising, administering to said patient a lithium source and a choline source, wherein:
   (a) said lithium source and said choline source are each periodically administered in amounts effective to reduce or eliminate the symptoms of said disorder; and
   (b) said administration is continued during both the manic and depressive phase of said disorder.

2. A method according to claim 1, wherein said choline source is a salt of choline.

3. A method according to claim 1, wherein said choline source provides a dose of about 50 mg of free choline per kg body weight per day.

4. A method according to claim 1, wherein said patient receives a dose of between about 2 and about 8 grams of free choline per day.

5. A method according to claim 1, which further comprises measuring the choline levels present in the brain of said patient using magnetic resonance spectroscopy.

6. The method of claim 1, wherein said disorder is lithium refractory bipolar disorder.

7. The method of claim 1, wherein said patient suffers from rapid cycling bipolar disorder.

8. The method of claim 3, wherein said lithium source and said choline source are administered orally.

9. The method of claim 4, wherein said lithium source and said choline source are administered orally.

10. The method of claim 2, wherein said salt of choline is choline bitartrate.

11. A method for treating bipolar disorder in a patient, who is receiving thyroid medication, which comprises:
    (a) administering to said patient a lithium source concomitantly with a choline source, with a relative amount of each that is effective to reduce or eliminate the symptoms associated with said disorder; and
    (b) concomitantly reducing or eliminating said thyroid medication.

12. A method according to claim 11, wherein said thyroid medication is thyroxine.

13. A method according to claim 11, wherein said choline source provides a dose of about 50 mg of free choline per kg body weight per day.

14. A method according to claim 11, wherein said patient receives a dose of between about 2 and about 8 grams of free choline per day.

15. The method of claim 13, wherein said lithium source and said choline source are administered orally.

16. The method of claim 14, wherein said lithium source and said choline source are administered orally.

17. The method of claim 11, wherein said choline source is a salt of choline.

18. The method of claim 17, wherein said salt of choline is choline bitartrate.

* * * * *